United States Patent
Pfauch et al.

(10) Patent No.: US 9,091,570 B2
(45) Date of Patent: Jul. 28, 2015

(54) RETRACTABLE ASSEMBLY

(75) Inventors: Thomas Pfauch, Leipzig (DE);
Hermann Straub, Rottenburg (DE);
René Kündscher, Radeburg (DE);
Rainer Schlereth, Neuss (DE)

(73) Assignee: ENDRESS + HAUSER CONDUCTA GESELLSCHAFT FUR MES- UND REGELTECHNIK MBH + CO. KG, Gerlingen (DE)

(*) Notice: Subject to any disclaimer, the term of this patent is extended or adjusted under 35 U.S.C. 154(b) by 248 days.

(21) Appl. No.: 13/568,880

(22) Filed: Aug. 7, 2012

(65) Prior Publication Data
US 2013/0036843 A1 Feb. 14, 2013

(30) Foreign Application Priority Data
Aug. 8, 2011 (DE) .......... 10 2011 080 579

(51) Int. Cl.
*G01D 11/24* (2006.01)
*G01N 27/28* (2006.01)

(52) U.S. Cl.
CPC ............ *G01D 11/245* (2013.01); *G01N 27/283* (2013.01)

(58) Field of Classification Search
CPC .............................. G01D 11/245; G01D 11/30
See application file for complete search history.

(56) References Cited

U.S. PATENT DOCUMENTS

| | | | |
|---|---|---|---|
| 7,117,757 B2 * | 10/2006 | Bellis, Jr. .............. | 73/866.5 |
| 7,272,983 B2 * | 9/2007 | Caderas .............. | 73/866.5 |
| 7,594,449 B2 | 9/2009 | Tottewitz | |
| 2009/0214387 A1 | 8/2009 | Straub | |
| 2011/0189050 A1 | 8/2011 | Schlereth | |
| 2011/0236962 A1 | 9/2011 | Loebbert | |
| 2011/0290045 A1 | 12/2011 | Hanko | |

FOREIGN PATENT DOCUMENTS

| | | |
|---|---|---|
| DE | 102005036865 A1 | 2/2007 |
| DE | 102005051279 A1 | 5/2007 |
| DE | 102005051279 B4 | 5/2007 |
| DE | 202007006784 U1 | 10/2007 |
| DE | 102006022983 A1 | 11/2007 |
| DE | 102006048898 A1 | 4/2008 |
| DE | 102007034268 B3 | 10/2008 |
| DE | 102007030584 A1 | 1/2009 |
| DE | 102009020440 A1 | 12/2010 |
| DE | 102009033558 A1 | 1/2011 |

(Continued)

OTHER PUBLICATIONS

Intl Search Rpt, Nov. 29, 2012, European Patent Office, Munich.

*Primary Examiner* — Paul West
(74) *Attorney, Agent, or Firm* — Bacon & Thomas, PLLC

(57) ABSTRACT

A retractable assembly, comprising: a housing; a media connection with complementary connecting means; an immersion tube; and a probe provided in the immersion tube. The probe has a probe head on its end facing the medium, wherein, in the service position, the probe head is arranged within a treatment chamber formed in the housing, wherein the immersion tube is divided into three regions, and, indeed, a upper region facing away from the containment, a middle region, on which a sealing system is provided, and a lower region facing the containment, wherein the sealing system is so embodied that in no position of the immersion tube does an exchange of medium or impurities from the drive to the treatment chamber, or vice versa, occur.

20 Claims, 7 Drawing Sheets

(56) References Cited

FOREIGN PATENT DOCUMENTS

| | | |
|---|---|---|
| DE | 102009045472 A1 | 4/2011 |
| DE | 102009045579 A1 | 4/2011 |
| DE | 102010001391 A1 | 8/2011 |
| DE | 102010001779 A1 | 8/2011 |
| DE | 102010001876 A1 | 8/2011 |
| DE | 102010028572 A1 | 11/2011 |
| DE | 102010029029 A1 | 11/2011 |
| EP | 0882896 A1 | 12/1998 |
| EP | 1750121 A1 | 2/2007 |
| EP | 1752763 A1 | 2/2007 |
| EP | 2019312 A2 | 1/2009 |
| EP | 2251650 A2 | 11/2010 |
| EP | 2278312 A1 | 1/2011 |
| WO | 2004023127 A1 | 3/2004 |
| WO | 2007048821 A2 | 5/2007 |
| WO | 2011042241 A1 | 4/2011 |
| WO | 2011138158 A1 | 11/2011 |

\* cited by examiner

RETRACTABLE ASSEMBLY

TECHNICAL FIELD

The invention relates to a retractable assembly.

BACKGROUND DISCUSSION

Retractable assemblies are widely used in analytical measurements technology. They serve to introduce probes into a process, and, therewith, into a medium, and then to withdraw such from the process, without interrupting the process as it is running, at pressures up to 10 bar and more. The probes are moved by means of a drive manually or automatically, for example, pneumatically, axially between a process position and a service position. In the service position, the probe is typically sealed from the medium.

Probes in the sense of this invention include probes with at least one accommodation for at least one sensor for measuring one or more process variables as well as sample takers, which withdraw from or feed to the process a determined amount of medium.

The fields of use of retractable assemblies for measuring physical or chemical process variables of a medium, e.g. of a fluid, especially a liquid, in process technology are vast. For determining process variables, sensors are used, wherein such sensors include, for example, pH-sensors, conductivity sensors, optical or electrochemical sensors for determining a concentration of a substance contained in the medium to be monitored, e.g. $O_2$, $CO_2$, certain types of ions, organic compounds, etc.

If the retractable assemblies are used for accommodating a sensor for determining at least one process variable, the sensor in the service position can be checked, calibrated, cleaned and/or replaced, wherein the sensor, in such case, is located in a treatment chamber arranged in the housing of the retractable assembly.

If the retractable assemblies are used as sample takers, in the service position, the medium taken by the sample taker into the treatment chamber can be examined, forwarded and/or filled, or the sample taker can be checked, cleaned and/or replaced. If one or more media need to be added to the process, in the service position, the sample taker can be filled with medium by means of a corresponding apparatus and then moved by the retractable assembly into the process.

Especially in pharmaceutical technology, however, for example, also in the chemicals and foods industries, retractable assemblies are used to monitor the manufacturing of products. The monitored processes must be kept very clean, i.e. free of impurities, partially even sterile, since a contamination of the process media with impurities, or, generally, with undesired media, influences the end product, and, thus, also the customers, or, depending on application, also the patients.

The use of retractable assemblies in sterile processes is problematic, since washing, or rinsing, media, e.g. calibration liquids, lubricants of the drive or other impurities can be allowed in no case to reach the process, because thereby the product safety or the patient safety would be endangered, as well as customer satisfaction damaged.

It is questionable that, in the case of known solutions, there is no reliable isolation between the treatment chamber and the drive. As a result thereof, in the presence of a lack of sealing in the region of the treatment chamber, medium can migrate unnoticed into the drive, which can lead to a failure of the drive;, moreover, it is not out of the question that medium can escape via the drive unit into the environment. Worse, however, is, that "unclean", certainly, however, unsterile materials can migrate or be dragged from the drive chamber or the environment into the treatment chamber and, thus, in the "clean", possibly even sterile, region of the retractable assembly. In the most unfavorable case, the unclean materials get from the treatment chamber into the process. Then, the medium becomes contaminated with undesired materials and cannot be used for patients or customers. Critical characterizing adjectives for the medium can include, for example: Valuable, expensive, combustible, etching or corrosive, poisonous, bio-endangering, radioactive, etc.

SUMMARY OF THE INVENTION

An object of the invention, therefore, is to provide a retractable assembly sealing system, which prevents an exchange of impurities between drive and treatment chamber.

The object is achieved by a retractable assembly, which comprises
  a housing,
  a media connection with complementary connecting means, wherein the connection is arranged on the housing and makes the retractable assembly connectable with a containment for a medium,
  an immersion tube, which is movable by a drive axially at least between two, preferably between three positions, and, indeed, a process position extending out of the housing, at least one intermediate position, and a service position in the housing, and
  a probe provided in the immersion tube, wherein the probe has a probe head on its end facing the medium, wherein, in the service position, the probe head is arranged within a treatment chamber formed in the housing, wherein the immersion tube is divided into three regions, and, indeed, an upper region facing away from the containment, a middle region, on which a sealing system is provided, and a lower region facing the containment, wherein the sealing system is so embodied that in no position of the immersion tube does an exchange of medium or impurities from the drive to the treatment chamber, or vice versa, occur.

In the above and following text sections, the position specifications "above", and, respectively "upper" or variations of these terms are to be understood as facing away from the containment or positioned farther away from such. Correspondingly, the position specifications "below", and, respectively "lower" or variations of these terms are to be understood as facing the containment or positioned nearer such.

The division of the immersion tube into three parts and the application of a sealing system in the middle region of the immersion tube prevents that impurities can migrate from the drive to the treatment chamber, and, in the worst case, to the medium, and vice versa.

An option provides that the respective regions of the immersion tube are of different materials. In this way, costs can be saved and/or materials used optimized for the respective purposes. Thus, the lower, process contacting region can be produced, for example, from a chemically very resistant material.

An especially advantageous embodiment provides that the sealing system is divided into three sections, and, indeed, an upper section, a middle section and a lower section.

In a preferred form of embodiment, in such case, the sealing system is composed of two seals, wherein the first seal is provided on the upper section of the sealing system, wherein the second seal is provided on the lower section of the sealing system, and the middle section of the sealing system has the length L. Both seals are located preferably on the outside of the immersion tube.

In an alternative embodiment, the sealing system is composed of one seal of at least length L, wherein the upper edge of the seal is associated with the upper section of the sealing system, wherein the lower edge of the seal is associated with the lower section of the sealing system, and wherein the region between the upper and the lower edges of the seal is associated with the middle section of the sealing system. The seal is located preferably on the outside of the immersion tube.

Through the application of two seals in the case of a division of the sealing system into three parts with a length L of the middle section, and, respectively, a single seal the length L, it is possible to prevent impurities migrating from the drive into the treatment chamber.

Preferably, a first connection to the treatment chamber is provided on the housing. The first connection is arranged in such a manner that washing, or rinsing, medium inflowing through the first connection rinses, cleans and/or sterilizes the lower section of the sealing system, when the immersion tube is located in the service position.

Sterilization in the sense of this invention includes the procedures, rinsing, flushing, washing, cleaning, disinfecting, decontamination, tyndallization, sterilization etc.

In an advantageous further development, the first connection is so embodied that its inner diameter is less than or equal to the length L.

Through the interaction of the first connection with an inner diameter less than or equal to the length L, the immersion tube divided into three parts and the sealing system divided into three parts, it is possible that in the service position the lower region of the immersion tube, the lower section of the sealing system, the treatment chamber and all regions of the probe located in the treatment chamber, especially the probe head, are washed, or rinsed and correspondingly cleaned and/or sterilized, which is viewed as especially advantageous. Furthermore, an option is to introduce a calibration medium into the treatment chamber, whereby the probe can be calibrated in the service position.

In a preferred form of embodiment, the first connection is so arranged that washing, or rinsing, medium inflowing through the first connection rinses, cleans and/or sterilizes the middle section of the sealing system, when the immersion tube is located in the intermediate position.

Should impurities be located in the middle section of the sealing system, these can be eliminated by the opportunity for sterilization in the intermediate position. Germs could be located in this section of the sealing system, since, in the service position, it is located above the first connection, and therewith faces the drive. This is potentially a contaminated region.

In an advantageous form of embodiment, a leakage bore is provided through the housing, wherein a detection unit is associated with the leakage bore, wherein the leakage bore is so arranged that the detection unit detects a malfunctioning of the upper section of the sealing system, when the immersion tube is located in the service position and washing, or rinsing, medium flows through the first connection or the first connection is supplied with pressure.

With the retractable assembly of the invention, the proposed sealing system prevents impurities migrating from the drive to the treatment chamber. Problematic is when, due to material fatigue, etc., the sealing system no longer functions flawlessly. Because of this, it is especially advantageous that a possible malfunctioning of the upper section of the sealing system can be detected and corresponding countermeasures can be taken.

In a desirable further development, a second connection to the treatment chamber is provided on the housing. The second connection is arranged in such a manner that medium squeezed in the case of axial movement of the immersion tube from the service position into the process position escapes through such connection. The squeezed medium can, in such case, be both liquid as well as also gas, e.g. air. Thus, it is assured that the immersion tube can move from the service position into the process position. If the immersion tube is located in the service position, washing, or rinsing, medium, which was introduced through the first connection into the treatment chamber, can be drained out through the second connection.

In a preferred embodiment, a detection unit is associated with the second connection, which detects malfunctioning of the lower section of the sealing system, when the immersion tube is located in the intermediate position and washing, or rinsing, medium flows through the first connection or the first connection is supplied with pressure.

Thus, it is also assured that a defect of the lower section of the sealing system is detected, which is viewed as especially advantageous. Possible defects of the middle section of the sealing system act directly either on the upper or the lower section and can likewise be detected. Thus, general detection of malfunctioning of the sealing system is possible.

In order to lock the immersion tube in the intermediate position, a locking element, a self-limiting drive or a automatically operating mechanism is provided.

Thus, it can be assured that the immersion tube resides safely in the intermediate position and the described steps, such as e.g. cleaning and sterilization of the middle section of the sealing system, can be performed.

In an advantageous further development, a rinsing chamber is provided, which is arranged in the housing below the treatment chamber.

Together with the treatment chamber, there are now two different chambers available for performing work on the probe. Examples include the sterilization or calibration of the probe in the treatment chamber.

In a preferred form of embodiment, at least one connection is provided to the rinsing chamber on the housing. Such connection is so embodied that washing, or rinsing, medium flowing through the connection rinses, cleans and/or sterilizes the rinsing chamber.

Into the rinsing chamber is introduced, for example, a washing, or rinsing, medium, which behaves uncritically relative to the medium located in the containment as well as relative to the washing, or rinsing, medium or calibration medium located in the treatment chamber. "Uncritically" means it is biologically and/or chemically and/or physically neutral relative to the medium in the treatment chamber. The inflowing washing, or rinsing, medium has, for example, a known and well defined pH- and/or conductivity value.

If leakage occurs in the region of the seal between the two chambers, this means that the medium from the treatment chamber is migrating into the rinsing chamber and mixing with washing, or rinsing, medium located there. If there is a leakage in the region of the process-side seal, this means that medium from the process is migrating into the rinsing chamber and mixing there.

This has the result that a property of the rinse or washing medium in the rinsing chamber changes. This change of a property of the rinse or washing medium is registered by means of a measuring apparatus, which is arranged outside of the housing and which is in connection with the connection to the rinsing chamber, i.e. the washing, or rinsing, medium running from the rinsing chamber is checked as regards one or more characteristic properties. If, now, a measured property of the rinse or washing medium from the rinsing chamber changes, leakage of a seal can be deduced.

In summary, it can be stated that all safety-critical seals of the retractable assemblies of the invention can be monitored for possible malfunctioning and so timely corresponding countermeasures can be brought into play.

BRIEF DESCRIPTION OF THE DRAWINGS

The invention will now be explained in greater detail based on the appended drawing, the figures of which show as follows:

FIG. 1b is a detail view of the sealing system of FIG. 1a;

FIG. 4b is a detail view of the alternative sealing system of FIG. 4a; and

DETAILED DISCUSSION IN CONJUNCTION WITH THE DRAWINGS

Figure 1A:
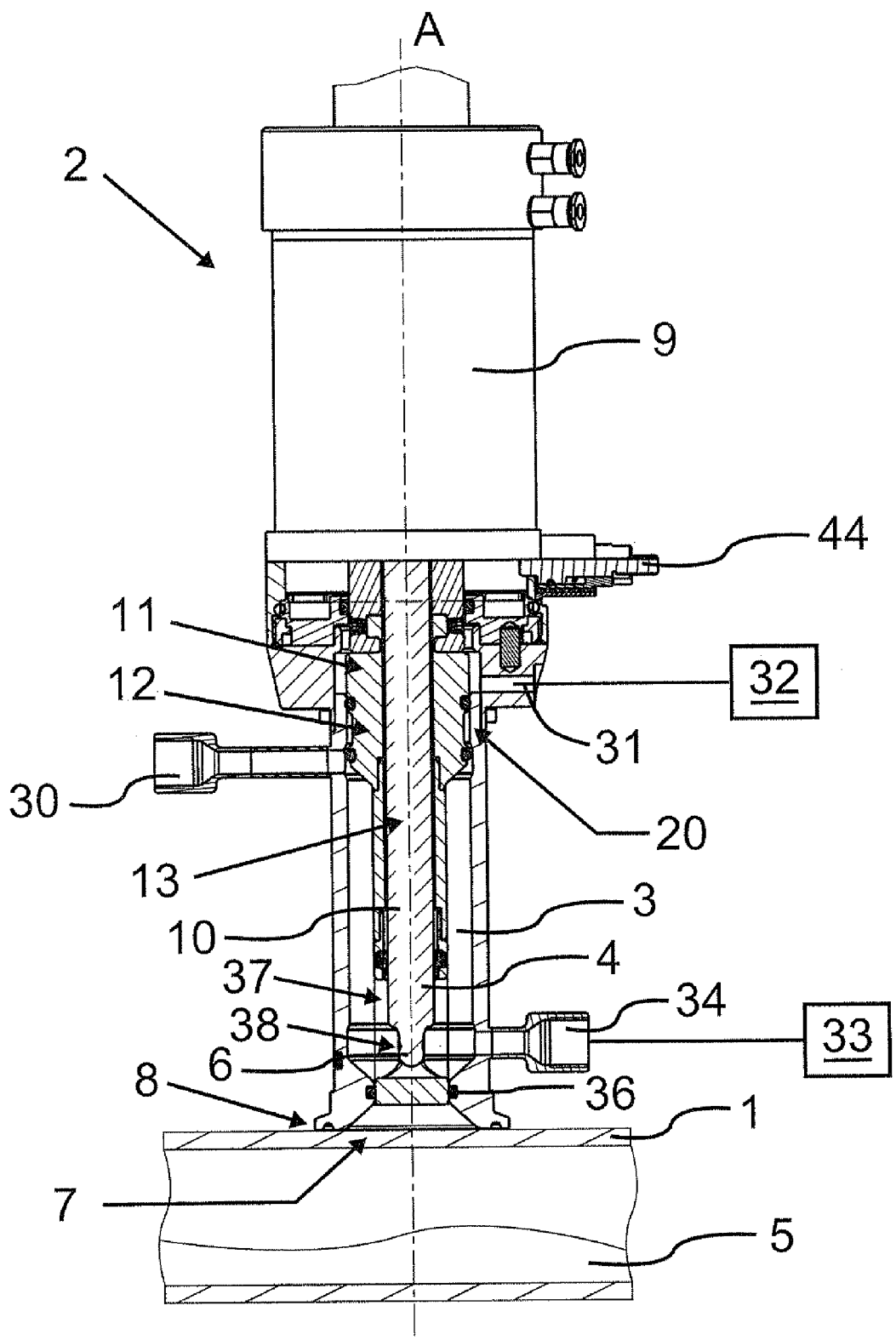
FIG. 1a is a cross section through a retractable assembly of the invention in the service position.

In the figures, equal features are provided with equal reference characters.

FIG. 1a shows a housing 2, which is connected with a containment 1 by means of a media connection 7 with complementary connecting means 8. This can be accomplished, for example, by way of a flange connection, etc. Located in the containment 1 is a medium 5. A containment 1 in the sense of this invention is a container, vessel, pipeline etc. Housing 2 has usually a cylindrical shape and is made, for example, of stainless steel or a resistant synthetic material, or plastic, such as polyetheretherketone (PEEK).

Guided within the housing 2 is an immersion tube 10, which can be displaced axially in the direction of the central axis A toward the containment 1, and, respectively, away from the containment 1. Central axis A coincides with the cylindrical symmetry axis of the housing 2, the cylindrical symmetry axis of the connection 7 to the medium, the cylindrical symmetry axis of the immersion tube 10, the cylindrical symmetry axis of the probe 4 and the cylindrical symmetry axis of the treatment chamber 3.

The shifting the immersion tube 10 is effected manually or automatically, for example, by a pneumatic or electrical drive 9. An automatic drive is not described here in detail. Its operation is, however, known, for example, from DE 10 2005 051 279 B4.

The immersion tube 10 is divided into three regions: An upper region 11, an middle region 12, on which a sealing system 20 (FIG. 1b) is provided and a lower region 13. The individual regions 11, 12, 13 of the immersion tube can be produced especially from different materials and are connected with one another by welding, screwing together, etc. For example, the lower, process contacting region can be manufactured from a very resistant material, such as PEEK or a suitable alloy.

Figure 1B:
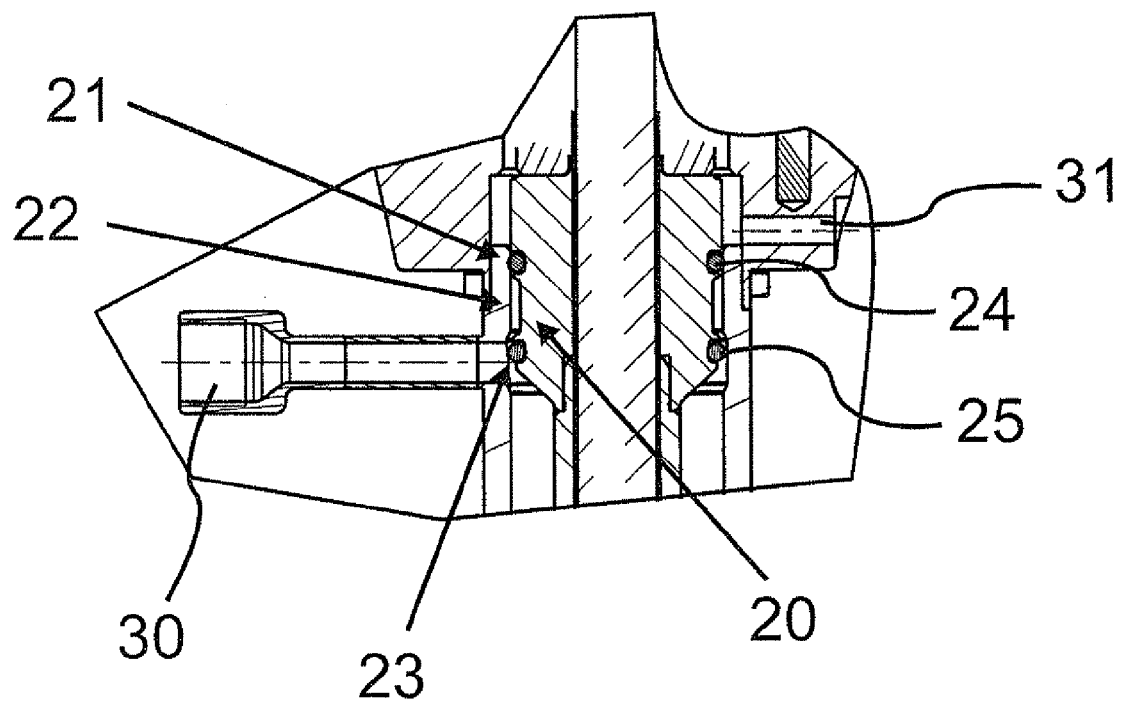

As shown in FIG. 1b, sealing system 20 is divided into three sections, and, indeed, an upper section 21, a middle section 22 and a lower section 23. The middle section 22 has a length L. In a first form of embodiment, the upper section 21 has a first seal 24 and the lower section 23 a second seal 25. The seals 24, 25 are arranged on the outside of the immersion tube 10 and are embodied, for example, as O-rings.

A probe 4 (FIG. 1) is, by way of a seat not described in greater detail, connected, for example, by a screwed connection, with the immersion tube 10. Located in the interior of the housing 2, coaxially with the immersion tube 10, is the treatment chamber 3. Seal 36 seals the probe 4 in the treatment chamber 3 relative to the medium 5.

In the form of embodiment shown in FIGS. 1 to 5, the probe is embodied as a sensor, with which physical and/or chemical process variables of the medium 5 can be determined. In this regard, there is located on the medium 5 facing end of the probe 4 a probe head 6.

On its lower end, the immersion tube 10 has surrounding the probe head 6 a protective cylinder 37, which has spaced from the external end a windowed region with openings 38. The probe 4 is held in such a manner in the immersion tube 10, that the probe head 6 is arranged within the protective cylinder 37, and the medium 5, into which the protective cylinder 37 immerses, comes in contact with the probe head 6 through the openings 38.

Probe head 6 has a measuring transducer (not shown), which produces, correlated with the process variable to be measured, a signal, which resides first in the probe head 6 and, in given cases, is conditioned there by a measuring electronics (not shown) and thereafter forwarded from the probe head 6 to a superordinated unit, for example, a measurement transmitter. The superordinated unit is connected e.g. by means of a galvanically decoupled interface (operating inductively, capacitively or optically) with the probe head 6 by an adapter (not shown), e.g. a plugged connection. Also possible are forms of embodiment with a sensor having a galvanic connection.

Process variables, which can be registered with the probe 4, include, for example, pH-value, also via ISFET, redox-potential, absorption of electromagnetic waves in the medium 5, for example, with wavelengths in the UV-, IR-, and/or visible region, oxygen content, conductivity, turbidity, concentration of metal and/or non-metal substances and temperature.

In an alternative form of embodiment (not described here in greater detail), the probe 4 is embodied as a sample taker. In principle, the sample taker withdraws by means of a corresponding apparatus on the probe head 6, e.g. a removal element, medium 5 from the containment 1. In such case, the immersion tube 10 with the sample taker is moved by the drive 9 into, and out of, the medium 5 in the containment 1. The sampled medium 5 can then be examined, forwarded and/or transferred into other containments.

In a variation, the sample taker introduces one or more media by means of a corresponding apparatus on the probe head 6, e.g. a feeding element, into the containment 1. In such case also, the immersion tube 10 with the sample taker is moved by the drive 9 into, and out of, the containment 1. The fed medium can possibly enter into a chemical reaction with the medium 5 located in the containment 1, mix with medium 5, dissolve something, emulsify, etc.

Located on housing 2 is a first connection 30 to the treatment chamber 3. Connection 30 has an inner diameter less than or equal to the length L. Through the connection 30 can flow washing, or rinsing, medium into the treatment chamber 3 for rinsing, cleaning, calibration, sterilization and/or for purging, pressure emptying, sucking out, etc. Options include standard pressure, positive pressure as well as also subpressure operating modes of the rinse or washing medium. The inflowing washing, or rinsing, medium can be, for example, superheated steam with a temperature greater than 80° C., especially greater than 100° C., for example, 120° C. It can be introduced under pressure. For sterilizing, the hot washing, or rinsing, medium is introduced into the treatment chamber 3 for a predetermined period of time, which can lie between 20 and 30 minutes.

Via a second connection 34, the washing, or rinsing, medium can drain from the treatment chamber 3. Associated with the second connection 34 is a detection unit 33, for example, a pressure- or liquid sensor. First and second connections 30, can be positioned radially on different sides; forms of embodiment, in the case of which the connections 30, 34 are located radially on the same side, are, however, options too. The connection 30 is positioned axially above the connection 34.

Furthermore, there is a leakage bore 31 located on the housing 2. Associated with the leakage bore 31 is a detection unit 32, for example, a pressure- or liquid sensor. The leakage bore 31 can be connected selectively with sterile/clean vessels.

The present invention has a number of positions of the immersion tube 10: A retracted, service position shown in FIGS. 1*a* and 4*a*, an intermediate position shown in FIG. 2 and a run out, process position shown in FIG. 3. In the run out, process position, the immersion tube 10 is located partially in the containment 1. In the retracted, service position, the immersion tube 10 is located in the interior of the housing 2. The connection 30 is so positioned on the housing 2 that the sealing system 20 in the service position is located at the same axial position. In the intermediate position, the immersion tube 10 is located in a position between completely retracted and completely run out.

If, in the service position (FIG. 1*a*), washing, or rinsing, medium is sent through the connection 30 into the treatment chamber 3, the lower region 13 of the immersion tube 10 is washed, or rinsed, by the washing, or rinsing, medium and correspondingly cleaned and/or sterilized. In the form of embodiment illustrated in FIG. 1*a* and enlarged in FIG. 1*b*, also the lower seal 25 is washed, or rinsed, and correspondingly cleaned and/or sterilized. Furthermore, in this position of the immersion tube 10, the treatment chamber and all regions of the probe 4 located in the treatment chamber 3, especially the probe head 6, are cleaned and/or sterilized. Inflowing washing, or rinsing, medium can drain through the connection 34 back out of the treatment chamber 3. Typically, the retractable assembly is so installed that the central axis of the retractable assembly has an inclined position of 15° to 75° relative to the horizontal.

Furthermore, an option provides that the probe 4 is calibrated through the use of calibration medium inflowing through connection 30. During the calibration procedure, the connection 34 is closed by a system associated with the connection 34, e.g. a valve (not shown), which is opened after terminating the procedure, in order to drain the calibration medium away.

In the service position of the immersion tube 10, a malfunctioning of the upper section 21 of the sealing system 20, especially a malfunctioning of the upper seal 24, can be detected by the detection unit 32 associated with the leakage bore 31. If the upper section 21 of the sealing system 20, especially the upper seal 24, is intact, no liquid or pressure drop is measured by the detection unit 32.

Figure 2:
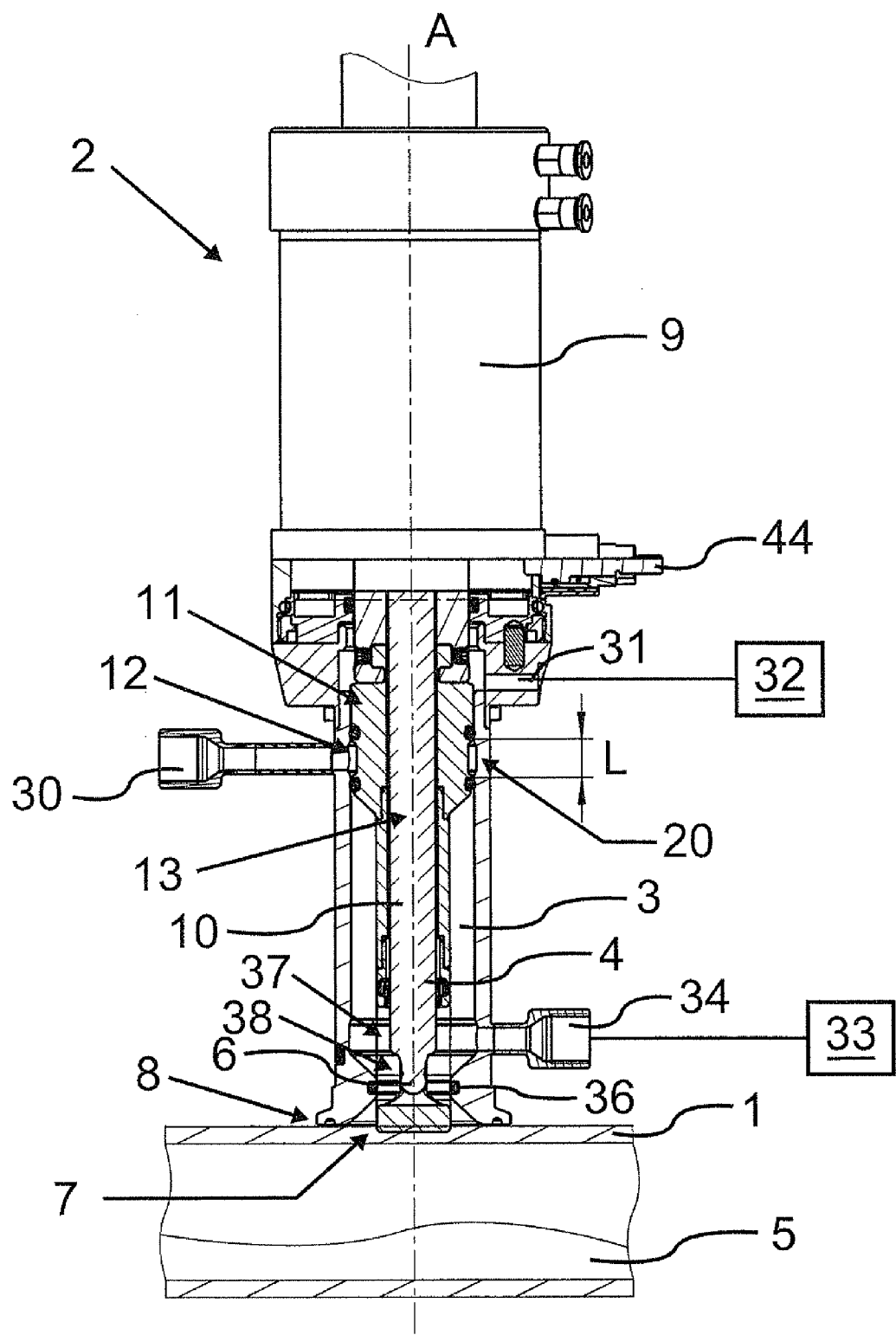
FIG. 2 is a cross section through the retractable assembly in the intermediate position.

The drive moves the immersion tube 10 from the service position into the intermediate position; see FIG. 2. The immersion tube is locked in the intermediate position, for example, by a locking element (locking bolt), a self-limiting drive or a corresponding automatically operating mechanism (in the drive).

In the intermediate position in FIG. 2, the upper seal 24 is located above the connection 30 and the lower seal 25 below the connection 30. In this way, there is assured a sealing of the lower region 13 of the immersion tube 10, and therewith the treatment chamber 3, as well as of the upper region 11 of the immersion tube 10. If, now, washing, or rinsing, medium is introduced through the connection 30, the middle section 22 of the sealing system 20 is cleaned and sterilized. A defect of the lower section 23 of the sealing system 20, especially a malfunctioning of the lower seal 25, can now be detected by the detection unit 33 associated with the second connection 34. If the lower section 23 of the sealing system 20, especially the lower seal 25, is intact, then no liquid or pressure drop is measured by the detection unit 33.

If the immersion tube 10 is moved by the drive 9 further downwards, i.e. in the direction of containment 1, the medium, for example, rinsing liquid or air, located in the treatment chamber 3 escapes through the connection 34. Through the movement of the immersion tube 10 downwards, the treatment chamber 3 becomes smaller in volume. In the case of oppositely moving movement of the immersion tube upwardly, from the process position into the service position via the intermediate position, the volume of the treatment chamber is regained. Medium, especially air, which has entered into the pressure chamber 35 during occupation of the process position, can escape through the leakage bore 31.

Figure 3:
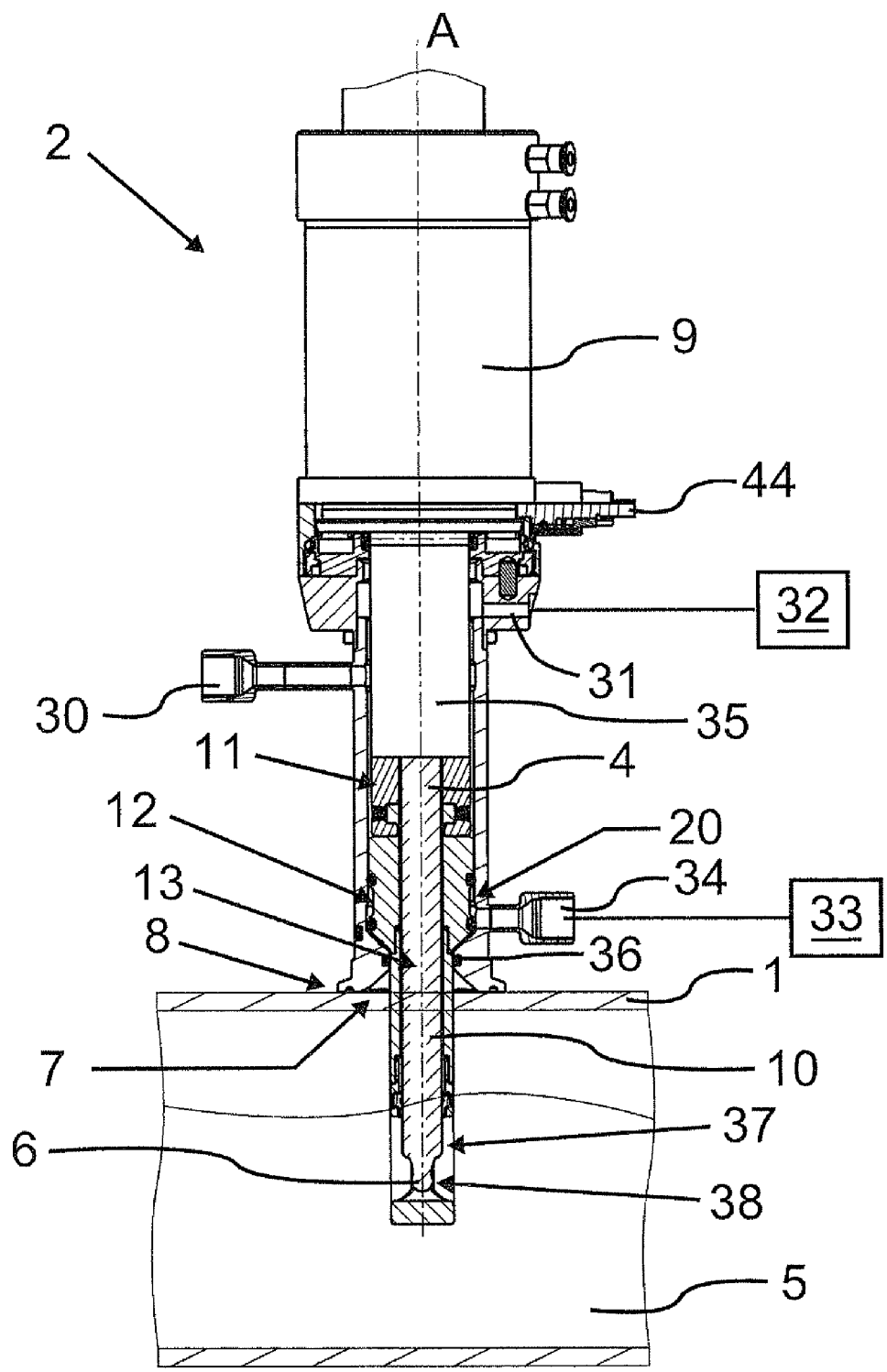
FIG. 3 is a cross section through the retractable assembly in the process Position.

In the process position in FIG. 3, the sealing system 20 is located at the height of the connection 34, above the seal 36. Through the connection 34, thus, the lower section 23 of the sealing system 20, especially the lower seal 25, can be cleaned and sterilized.

It is, thus, assured in each position of the immersion tube 10 that no impurities can get from drive 9 to the containment 1.

With little technical effort, a further option is that also the pressure chamber 35 can be rinsed, cleaned and sterilized through washing, or rinsing, medium charged through the connection 30.

Figure 4A:
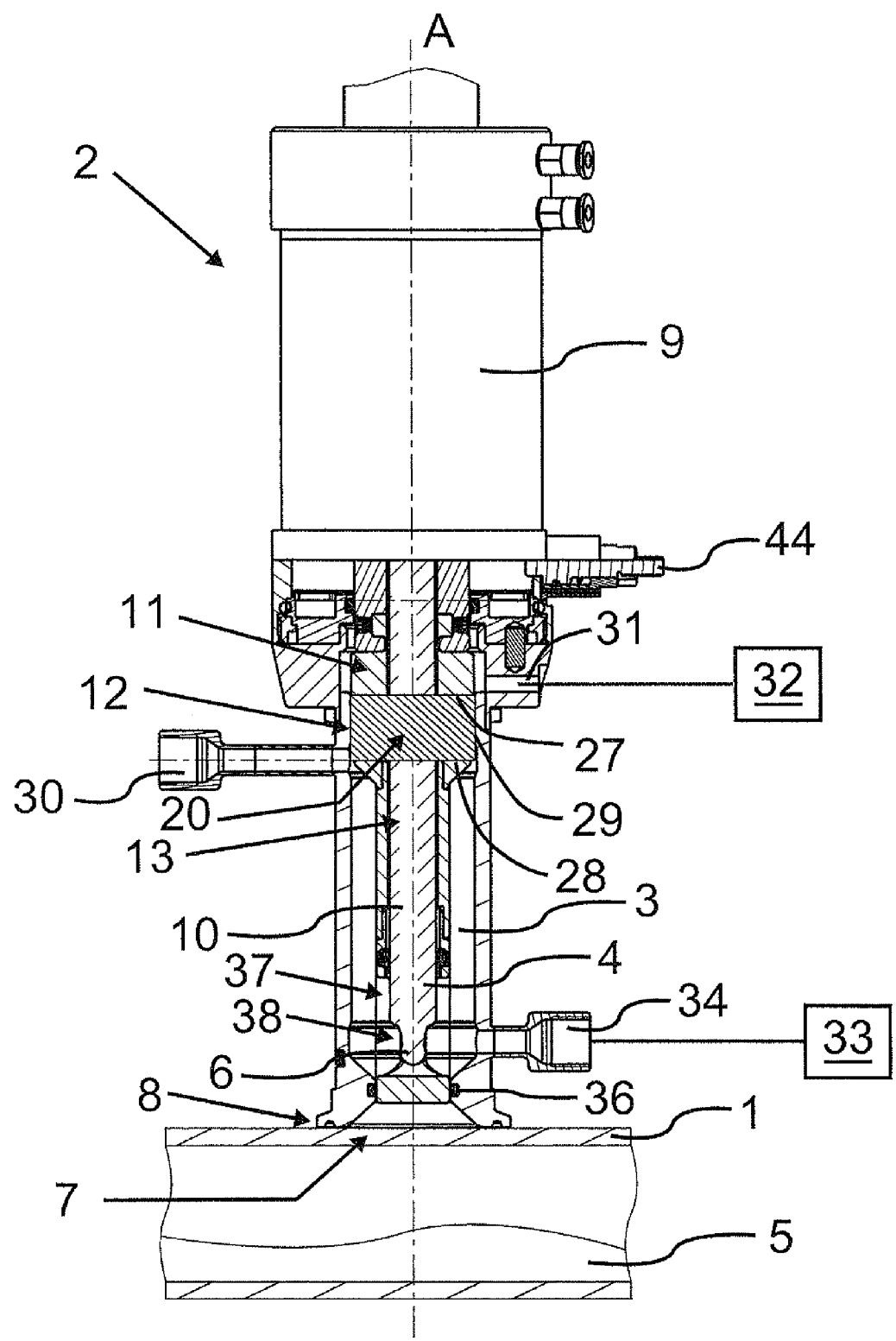
FIG. 4a is a cross section through the retractable assembly in the service position with an alternative sealing system.
Figure 4B:
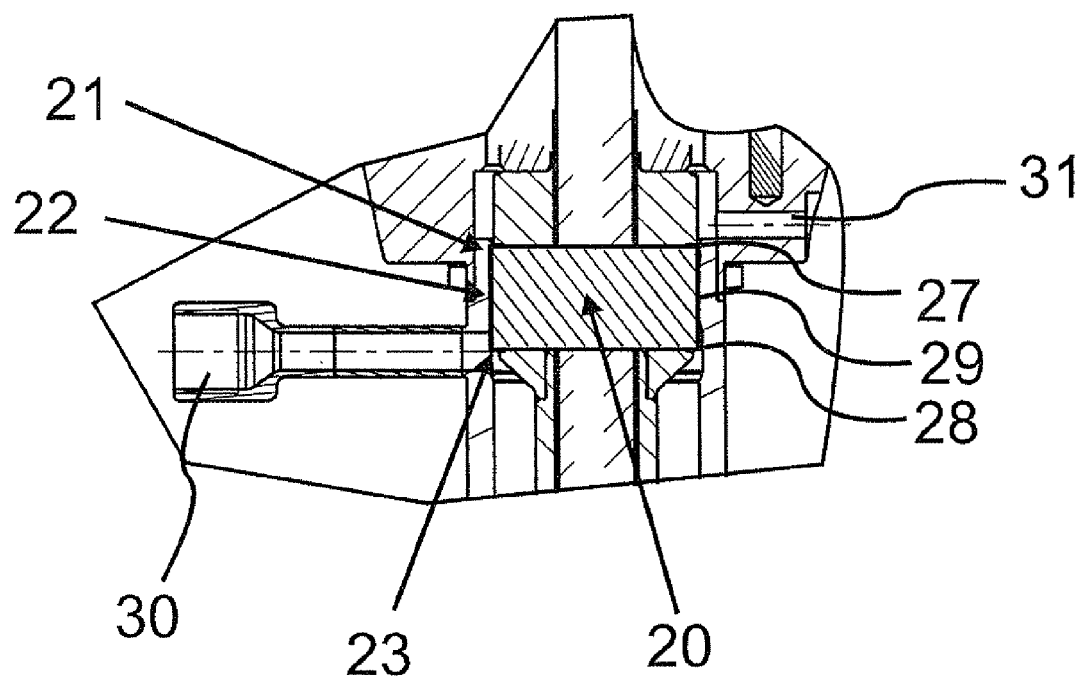

FIG. 4*a* shows an alternative embodiment of the sealing system 20. In this embodiment, composed the sealing system 20 is of only one seal 26 having at least the length L. Seal 26 has an upper edge 27 and a lower edge 28. FIG. 4*b* shows an enlarged view of the alternative sealing system 20. Seal 26 is arranged on the outside of the immersion tube 10.

Fundamentally, the alternative sealing system of FIGS. 4*a/b* functions equally as the sealing system of FIGS. 1*a/b*, only that in this case one seal of length L is used instead of two seals separated by a distance L.

Figure 5:
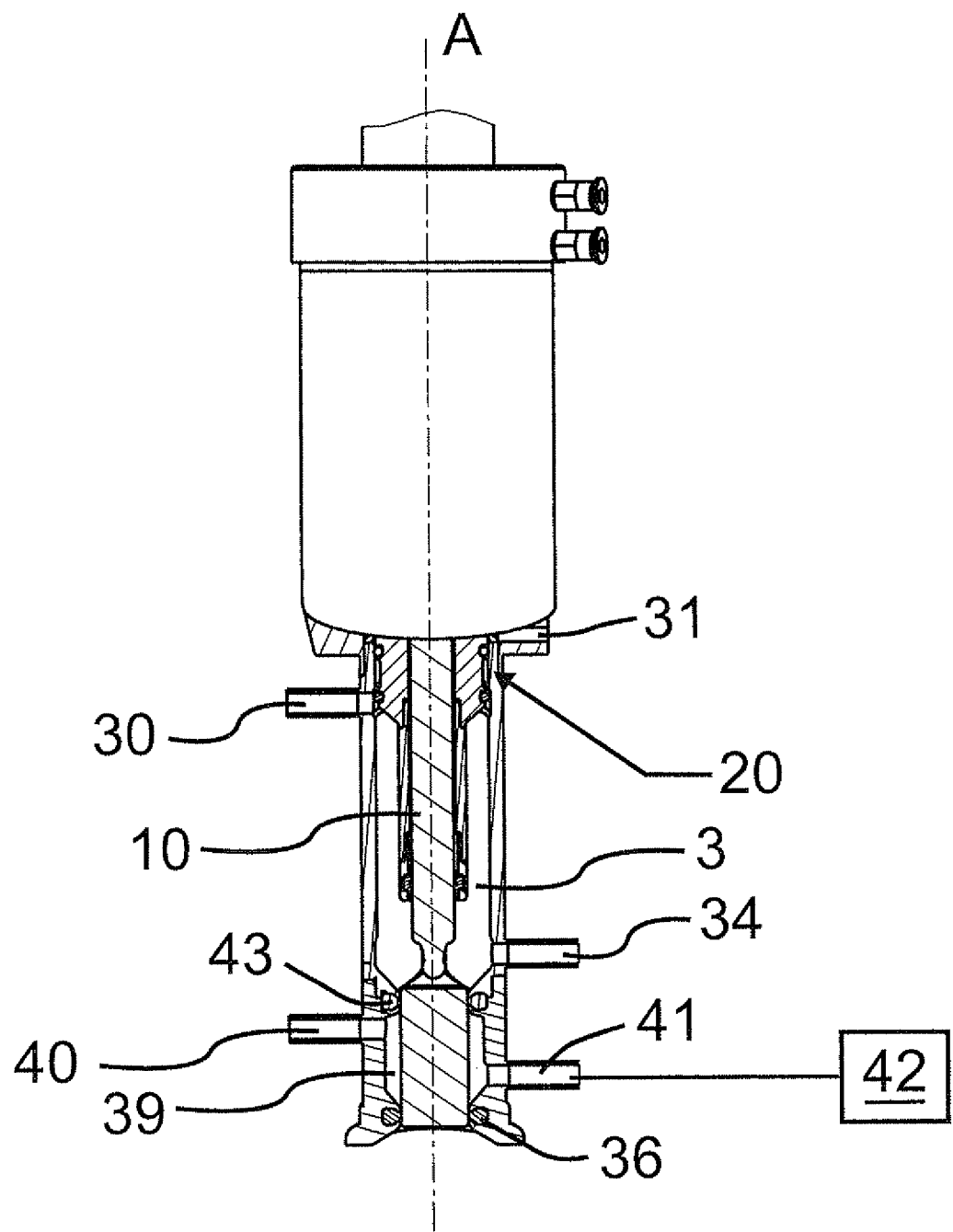
FIG. 5 is a cross section through the retractable assembly with additional rinsing chamber.

FIG. 5 shows the retractable assembly of the invention with a rinsing chamber 39 located below the treatment chamber 3. Otherwise, the retractable assembly has the same features as described above. The sealing system 20 can have two seals as described in FIGS. 1*a/b* and shown in FIG. 5, or a single seal as described for FIGS. 4*a/b*.

Rinsing chamber 39 and treatment chamber 3 are sealed relative to one another by a seal 43. On the process-side, rinsing chamber 39 is sealed by a seal 36. Rinsing chamber 39 has two connections 40, 41, wherein a detection unit 42 is associated with the connection 41.

Through the connection 40, washing, or rinsing, medium is continuously charged into the rinsing chamber 39. The washing, or rinsing, medium has known and well defined properties, e.g. pH-value or conductivity. If there is now a leakage at one of the seals 36, 43, medium 5 from the containment 1 or the treatment chamber 3 leaks into the rinsing chamber 39. Through the mixing, the washing, or rinsing, medium changes and the detection unit 42 associated with the connection 41 can detect this change of a property of the rinse or washing medium.

It is, furthermore, an option that the washing, or rinsing, medium, which is charged through the connection 40 into the rinsing chamber 39, has cooling or heating properties. Since a sterilization procedure of the treatment chamber 3 and/or the probe 4 is usually performed with superheated steam, the treatment chamber 3 and the probe 4 have an increased temperature after such a procedure. If, now, cooling medium is charged through the rinsing chamber 39 located under the treatment chamber 3, then rinsing chamber 39 is cooled off. This can be advantageous, especially when the probe 4 is not permitted to enter containment 1 with increased temperature, for example, in order not to compromise process safety. Through the described procedure, the downtime of the probe 4 is lessened and, thus, costs saved.

Furthermore, cooling of the rinsing chamber 39 by means of a rinse or washing medium prevents that during a rinsing, cleaning or sterilization of the treatment chamber 3 and/or probe 4, which usually involves increased temperature, the medium 5 located in the containment 1 is likewise heated (for example, by heat transfer) and, thus, in given cases, destroyed or functionally degraded (i.e. color, activity, yield, etc.).

The invention claimed is:

1. A retractable assembly, comprising:
a housing, having a treatment chamber;
a media connection with complementary connecting means, said media connection is arranged on said housing, and connects the retractable assembly with a containment filled with a medium;
a drive;
an immersion tube, which is movable by said drive axially at least between three positions, a process position extending out of said housing at least one intermediate position, and a service position in said housing; and
a probe provided in the immersion tube, wherein:
said probe has a probe head on its end facing the medium;
in the service position, said probe head is arranged within said treatment chamber formed in said housing;
said immersion tube is divided into three regions, an upper region facing away from the containment, a middle region, on which a sealing system is provided, and a lower region facing the containment;
said sealing system is divided into three sections, an upper section, a middle section and a lower section;
said sealing system is composed of two seals, the first seal is provided on the upper section of said sealing system, the second seal is provided on the lower section of said sealing system, and the middle section of the sealing system has a length L;
said first seal and said second seal are arranged on the outside of said immersion tube; and
said sealing system is so embodied that in no position of the immersion tube does an exchange of medium or impurities from said drive to said treatment chamber, or vice versa, occur.

2. The retractable assembly as claimed in claim 1, wherein:
a first connection to said treatment chamber is provided on said housing;
said first connection is arranged in such a manner that washing, or rinsing, medium inflowing through it rinses, cleans and/or sterilizes the lower section of said sealing system, when said immersion tube is located in the service position.

3. The retractable assembly as claimed in claim 2, wherein:
a second connection to said treatment chamber is provided on said housing;
said second connection is arranged in such a manner that medium squeezed in the case of axial movement of said immersion tube from said service position into said process position escapes through said second connection.

4. The retractable assembly as claimed in claim 1, wherein:
said first connection is so embodied that its inner diameter is less than or equal to the length L.

5. The retractable assembly as claimed in claim 1, wherein:
a first connection is so arranged that washing, or rinsing, medium inflowing through it rinses, cleans and/or sterilizes the middle section of said sealing system, when said immersion tube is located in said intermediate position.

6. The retractable assembly as claimed in claim 1, wherein:
a locking element, a self-limiting drive or an automatically operating mechanism is provided, which locks said immersion tube in said intermediate position.

7. The retractable assembly as claimed in claim 1, wherein:
a rinsing chamber is provided, which is arranged in said housing below said treatment chamber.

8. The retractable assembly as claimed in claim 7, wherein:
at least one connection to said rinsing chamber is provided on said housing;
said connection is so embodied that washing, or rinsing, medium flowing through said connection rinses, cleans and/or sterilizes said rinsing chamber.

9. A retractable assembly, comprising:
a housing, having a treatment chamber;
a media connection with complementary connecting means, said media connection is arranged on said housing and makes the retractable assembly connectable with a containment filled with a medium;
a drive;
an immersion tube, which is movable by said drive axially at least between two, preferably three positions, a process position extending out of said housing at least one intermediate position, and a service position in said housing; and
a probe provided in the immersion tube, wherein:
said probe has a probe head on its end facing the medium;
in the service position, said probe head is arranged within said treatment chamber formed in said housing;
said immersion tube is divided into three regions, an upper region facing away from the containment, a middle region, on which a sealing system is provided, and a lower region facing the containment;
said sealing system is so embodied that in no position of the immersion tube does an exchange of medium or impurities from said drive to said treatment chamber, or vice versa, occur;
a leakage bore is provided through said housing;
a detection unit is associated with said leakage bore; and
said leakage bore is so arranged that said detection unit detects a malfunctioning of an upper section of said sealing system, when said immersion tube is located in said service position and washing, or rinsing, medium flows through a first connection or a first connection is supplied with pressure.

10. A retractable assembly, comprising:
a housing, having a treatment chamber;
a media connection with complementary connecting means, said media connection is arranged on said housing and makes the retractable assembly connectable with a containment filled with a medium;

a drive;
an immersion tube, which is movable by said drive axially at least between two, preferably three positions, a process position extending out of said housing at least one intermediate position, and a service position in said housing; and a probe provided in the immersion tube, wherein:
said probe has a probe head on its end facing the medium;
in the service position, said probe head is arranged within said treatment chamber formed in said housing;
said immersion tube is divided into three regions, an upper region facing away from the containment, a middle region, on which a sealing system is provided, and a lower region facing the containment;
said sealing system is so embodied that in no position of the immersion tube does an exchange of medium or impurities from said drive to said treatment chamber, or vice versa, occur;
a first connection to said treatment chamber is provided on said housing;
said first connection is arranged in such a manner that washing, or rinsing, medium inflowing through it rinses, cleans and/or sterilizes a lower section of said sealing system, when said immersion tube is located in the service position, a second connection to said treatment chamber is provided on said housing;
said second connection is arranged in such a manner that medium squeezed in the case of axial movement of said immersion tube from said service position into said process position escapes through said second connection; and
associated with said second connection is a detection unit, which detects a malfunctioning of said lower section of said sealing system, when said immersion tube is located in said intermediate position and washing, or rinsing, medium flows through said first connection or said first connection is supplied with pressure.

11. A retractable assembly, comprising:
a housing, having a treatment chamber;
a media connection with complementary connecting means, said media connection is arranged on said housing and makes the retractable assembly connectable with a containment filled with a medium;
a drive; and
an immersion tube, which is movable by said drive axially at least between three positions, a process position extending out of said housing at least one intermediate position, and a service position in said housing; and
a probe provided in the immersion tube, wherein:
said probe has a probe head on its end facing the medium;
in the service position, said probe head is arranged within said treatment chamber formed in said housing;
said immersion tube is divided into three regions, an upper region facing away from the containment, a middle region, on which a sealing system is provided, and a lower region facing the containment;
said sealing system is divided into three sections, an upper section, a middle section and a lower section;
said sealing system is composed of one seal of at least length L;
an upper edge of said seal is associated with the upper section of said sealing system;
a lower edge of said seal is associated with the lower section of said sealing system;
a region between said upper and the lower edges of said seal is associated with said middle section of said sealing system;
said seal is arranged on the outside of said immersion tube; and
said sealing system is so embodied that in no position of the immersion tube does an exchange of medium or impurities from said drive to said treatment chamber, or vice versa, occur.

12. The retractable assembly as claimed in claim 11, wherein:
a first connection to said treatment chamber is provided on said housing;
said first connection is arranged in such a manner that washing, or rinsing, medium inflowing through it rinses, cleans and/or sterilizes said lower section of said sealing system, when said immersion tube is located in the service position.

13. The retractable assembly as claimed in claim 12, wherein:
a second connection to said treatment chamber is provided on said housing;
said second connection is arranged in such a manner that medium squeezed in the case of axial movement of said immersion tube from said service position into said process position escapes through said second connection.

14. The retractable assembly as claimed in claim 13, wherein:
associated with said second connection is a detection unit, which detects a malfunctioning of said lower section of said sealing system, when said immersion tube is located in said intermediate position and washing, or rinsing, medium flows through said first connection or said first connection is supplied with pressure.

15. The retractable assembly as claimed in claim 11, wherein:
said first connection is so embodied that its inner diameter is less than or equal to the length L.

16. The retractable assembly as claimed in claim 11, wherein:
said first connection is so arranged that washing, or rinsing, medium inflowing through it rinses, cleans and/or sterilizes said middle section of said sealing system, when said immersion tube is located in said intermediate position.

17. The retractable assembly as claimed in claim 11, wherein:
a leakage bore is provided through said housing;
a detection unit is associated with said leakage bore;
said leakage bore is so arranged that said detection unit detects a malfunctioning of said upper section of said sealing system, when said immersion tube is located in said service position and washing, or rinsing, medium flows through said first connection or said first connection is supplied with pressure.

18. The retractable assembly as claimed in claim 11, wherein:
a locking element, a self-limiting drive or an automatically operating mechanism is provided, which locks said immersion tube in said intermediate position.

19. The retractable assembly as claimed in claim 11, wherein:
a rinsing chamber is provided, which is arranged in said housing below said treatment chamber.

20. The retractable assembly as claimed in claim 19, wherein:
at least one connection to said rinsing chamber is provided on said housing;

said connection is so embodied that washing, or rinsing, medium flowing through said connection rinses, cleans and/or sterilizes said rinsing chamber.

* * * * *